United States Patent [19]

Chiang et al.

[11] 4,210,639

[45] Jul. 1, 1980

[54] 5'-DEOXY-5'-(ISOBUTYLTHIO)-3-DEAZAADENOSINE, METHOD OF MAKING SAME AND ITS ANTIVIRAL EFFECT ON ROUS SARCOMA VIRUS AND GROSS MURINE LEUKEMIA VIRUS

[75] Inventors: Peter K. Chiang, Kensington; Guilio L. Cantoni, Bethesda; John P. Bader, Rockville, all of Md.; William M. Shannon, Birmingham, Ala.; H. Jeanette Thomas, Birmingham, Ala.; John A. Montgomery, Birmingham, Ala.

[73] Assignee: The United States of America as represented by the Department of Health, Education and Welfare, Washington, D.C.

[21] Appl. No.: 937,704

[22] Filed: Aug. 29, 1978

[51] Int. Cl.$^2$ .................. A61K 31/70; C07H 19/16; C07H 17/00
[52] U.S. Cl. .................................. 424/180; 536/26; 536/24
[58] Field of Search .................. 536/26, 24; 424/180

[56] References Cited

FOREIGN PATENT DOCUMENTS 7717602  6/1977  France ........................................ 536/26

OTHER PUBLICATIONS

Montgomery, J., et al., J. Heterocyclic Chem., 14, 195 (1977).
Chiang, P., et al., Biochem. Biophys. Research Communications, 82 (2), 417 (1978).
Chiang, P., et al., Molecular Pharmacology, 13, 939 (1977).
Rowe, W., et al., Virology, 42, 1136 (1970).
Shannon, W., et al., Journal of the National Cancer Institute, 52 (1), 199 (1974).

*Primary Examiner*—Johnnie R. Brown
*Assistant Examiner*—Blondel Hazel
*Attorney, Agent, or Firm*—John S. Roberts, Jr.

[57] ABSTRACT

5'-Deoxy-5'-(isobutylthio)-3-deazaadenosine and a method for preparation of same. In the preparation, 3-deazaadenosine is utilized as a starting material and is chlorinated at the 5' position. Subsequently, the chloro group is converted to isobutylthio by reaction with isobutyl mercaptan in ethanol containing sodium methoxide giving the desired compound.

A most preferred starting material, i.e., 3-deazaadenosine, was prepared according to the method of Montgomery et al, *J. Heterocyclic Chem.*, 14:195 (1977). The key fusion of this process is 4,6-dichloroimidazo[4,5-c]pyridine with 1,2,3,5-tetra-O-acetyl-$\beta$-D-ribofuranose, which, after removal of protective groups and reductive dechlorination of the chlorine at 6, gives 3-deazaadenosine.

This new compound has good activity as an adenosylhomocysteine (AdoHcy) hydrolase inhibitor and has shown activity against Rous sarcoma virus (RSV) in chick embryo cells and Gross murine leukemia virus (Gross MLV) in mouse embryo cells, where the activity is as a non-competitive inhibitor of AdoHcy hydrolase showing A $K_i$ of 0.4 mM.

3 Claims, 2 Drawing Figures

INHIBITIONS OF AdoHcy HYDROLASE FROM COW LIVER BY: (O) 5'-DEOXY-5'-S-ISOBUTYL-ADENOSINE, (□) 9-[5'-DEOXY-5'-(METHYLTHIO)-β-D-ARABINOFURANOSYL] ADENINE, (●) 5'-DEOXY-5'-(ISOBUTYLTHIO)-3-DEAZAADENOSINE, (△) Nγ-ADENOSYL-α-γ-DIAMINOBUTYRIC ACID.

ANTI-VIRAL ACTIVITY OF 5'-DEOXY-5'-(ISOBUTYLTHIO)-3-DEAZAADENOSINE AGAINST GROSS MLV IN VITRO.

5'-DEOXY-5'-(ISOBUTYLTHIO)-3-DEAZAADENOSINE, METHOD OF MAKING SAME AND ITS ANTIVIRAL EFFECT ON ROUS SARCOMA VIRUS AND GROSS MURINE LEUKEMIA VIRUS

This invention relates to the compound, 5'-deoxy-5'-(isobutylthio)-3-deazaadenosine, and a method for preparation of same. In the preparation, 3-deazaadenosine is utilized as a starting material and is chlorinated at the 5' position. Subsequently, the chloro group is converted to isobutylthio by reaction with isobutyl mercaptan in ethanol containing sodium methoxide giving the desired compound.

A most preferred starting material, i.e., 3-deazaadenosine, was prepared according to the method of Montgomery et al, *J. Heterocyclic Chem.*, 14:195 (1977). The key fusion of this process is 4,6-dichloroimidazo[4,5-c]-pyridine with 1,2,3,5-tetra-O-acetyl-β-D-ribofuranose, which, after removal of protective groups and reductive dechlorination of the chlorine at 6, gives 3-deazaadenosine.

This new compound has good activity as an adenosylhomocysteine (AdoHcy) hydrolase inhibitor and has shown activity against Rous sarcoma virus (RSV) in chick embryo cells and Gross murine leukemia virus (Gross MLV) in mouse embryo cells, where the activity is as a non-competitive inhibitor of AdoHcy hydrolase showing a $K_i$ of 0.4 mM.

5'-Deoxy-5'-(isobutylthio)-3-deazaadenosine is a compound which is a copy of adenosine less the nitrogen at the 3 position and with an isobutylthio at the 5'-position. It has been found that this compound, 5'-deoxy-5'-(isobutylthio)-3-deazaadenosine, inhibits or suppresses the important reversible hydrolysis of S-adenosyl-homocysteine according to the following formula:

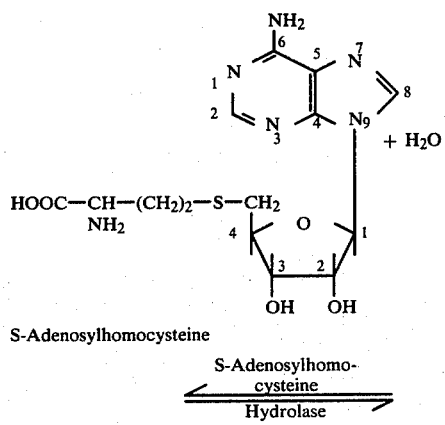

S-Adenosylhomocysteine $$\xrightarrow{\text{S-Adenosylhomocysteine Hydrolase}}$$

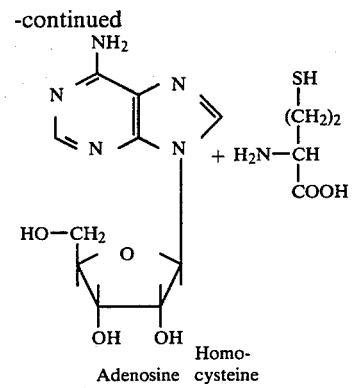

Adenosine   Homocysteine

PRIOR ART STATEMENT

Wallace P. Rowe, et al, *Virology*, 42:1136–1139 (1970).

William M. Shannon, et al, *Journal of the National Cancer Institute*, 52(1):199;14 205 (January 1974).

Peter K. Chiang, et al, *Molecular Pharmacology*, 13:939–947 (1977).

John A. Montgomery, et al, *J. Heterocyclic Chemistry*, 14:195 (1977).

Peter K. Chiang, et al, *Biochem. Biophys. Research Communications*, 82(2):417–423 (May 30, 1978).

Peter K. Chiang and Giulio L. Cantoni, "Levels of Adenosylmethionine and Adenosylhomocysteine in Livers of Rats Injected with 3-Deazaadenosine, Methionine and Nicotinamide," [to be published].

Henry H. Richards, Peter K. Chiang and Giulio L. Cantoni, "Adenosylhomocysteine Hydrolase: Crystallization of the Purified Enzyme and Its Properties," [to be published JBC].

It is known that the enzymatic transfer of the methyl group of S-adenosyl-L-methionine yields S-adenosyl-L-homocysteine as one of the products of the reaction. In eukaryotes the principal pathway for the metabolism of adenosylhomocysteine is its hydrolysis to L-homocysteine and adenosine by the action of an anzyme, adenosylhomocysteine hydrolase.

Adenosylhomocysteine (AdoHcy) has been found to inhibit competitively most of the methyltransferases which utilize adenosylmethionine as the methyl donor. Thus, it is further known that the regulation of adenosylhomocysteine hydrolase by various effectors can be of physiological importance in controlling biological methylations.

It has been further found that the present compound, 5'-deoxy-5'-(isobutylthio)-3-deazaadenosine, is a non-competitive inhibitor for AdoHcy hydrolase, with a $K_i$ of 0.4 mM. 5'-Deoxy-5'-(isobutylthio)-3-deazaadenosine is not hydrolyzed by AdoHcy hydrolase.

Adenosylmethionine (AdoMet) is known to participate as a methyl donor in many reactions of physiological importance. Adenosylhomocysteine (AdoHcy), the product of these methyl transfer reactions, is known to be a competitive inhibitor of these same reactions, and analogs or copies of AdoHcy with varying degrees of specificity can act as inhibitors of methylases. Among the known analogs of adenosine, 3-deazaadenosine was found to be the most potent inhibitor of AdoHcy hydrolase, and is nearly 100-fold more potent than 5'-deoxy-5'-S-isobutyl-adenosine as an inhibitor of this enzyme. The present compound, 5'-deoxy-5'-(isobutylthio)-3-deazaadenosine, is a compound which incorporates 3-deazaadenosine into a bioisostere of 5'-deoxy-5'-S-isobutyladenosine, both compounds being potent inhibitors of AdoHcy hydrolase and also antiviral antitumor agents well tolerated by cells.

It has also been found that this novel compound shows good antiviral against Rous sarcoma virus in chick embryo cells and Gross murine leukemia virus in mouse embryo cells. Additionally, it will reverse the malignant transformation induced by oncogenic virus and the experimental data is set out post in the examples and drawings.

EXAMPLE 1

Preparation of the Compound, 5'-Deoxy-5'-(Isobutylthio)-3-Deazaadenosine

Synthesis of Compound

Figure 1:
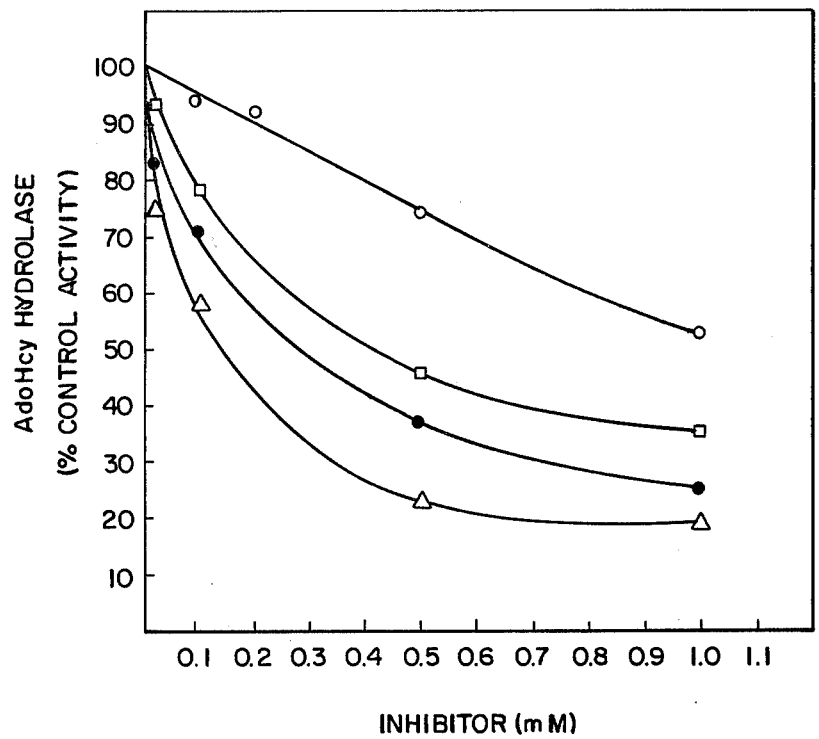
FIG. 1 shows the comparison of the inhibition of AdoHcy hydrolase from cow liver by 5'-deoxy-5'-S-isobutyladenosine, 9-[5'-deoxy-5'-(methylthio)-β-D-arabinofuranosyl]-adenine, 5'-deoxy-5'-(isobutylthio)-3-deazaadenosine, and Nγ-adenosyl-α,γ-diamino-butyric acid, with $I_{50}$'s of >1.0, 0.43, 0.28, and 0.14 mM, respectively. See Example 3.

5'-Deoxy-5'-(isobutylthio)-3-deazaadenosine was synthesized as follows:

3-Deazaadenosine (I), prepared by the procedure of Montgomery et al, *J. Heterocyclic Chem.*, 14:195–197 (1977), was chlorinated with thionyl chloride in hexamethylphosphoramide to give 5'-chloro-5'-deoxy-3-deazaadenosine, which on reaction with isobutyl mercaptan in ethanol containing sodium methoxide gave 5'-deoxy-5'-(isobutylthio)-3-deazaadenosine:

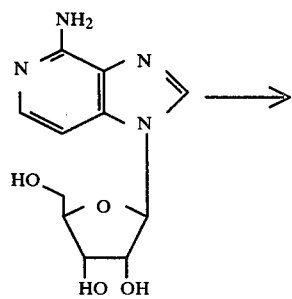

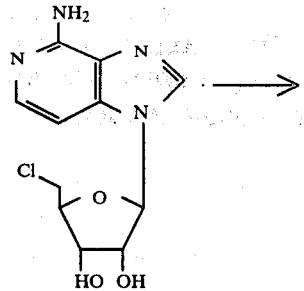

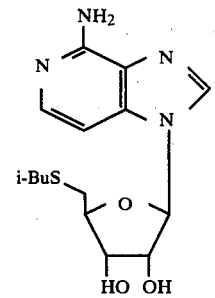

5'-Chloro-5'-deoxy-3-deazaadenosine (II). A solution of 3-deazaadenosine (1.89 mmol) in hexamethylphosphoramide (5 ml) containing thionyl chloride (0.75 ml) was kept for 20 h at ambient temperature and then poured into 20 ml of cold chloroform. The pH of the resulting solution was raised to 9 with concentrated ammonium hydroxide with cooling. Water (25 ml) was added with shaking and the aqueous layer removed and lyophilized to give a fluffy, yellow solid. This material was used without further purification.

5'-Deoxy-5'-(isobutylthio)-3-deazaadenosine (III). A solution of 1.89 mmol of crude 5'-chloro-5'-deoxy-3-deazaadenosine in 18.9 ml of 1 N sodium methoxide in absolute ethanol containing 2.71 ml (25 mmol) of isobutyl mercaptan was refluxed for 30 min. neutralized with glacial acetic acid, and evaporated to dryness in vacuo. The filtered chloroform extract was evaporated to dryness in vacuo. An aqueous solution of the residue was treated with 1.89 mmol of solid picric acid. Stirring and gentle heating produced a heavy crystalline precipitate. After refrigeration of the mixture for several hours, the solid was collected by filtration, washed with a small amount of cold water, and dissolved in methanol. The methanol solution was stirred with Dowex 1-X8 (carbonate) ion-exchange resin until it became colorless. The resin was filtered and washed several times with methanol and then water. The combined filtrate and washings was evaporated to dryness in vacuo. The residue crystallized from water and on drying in vacuo at 78° melted to a glass, yield 134 mg (21%); uv max in nm ($\epsilon \times 10^{-3}$): (0.1 N HCl) 263 (11.90), (pH 7) 264 (10.44), (0.1 N NaOH) 265 (10.86). TLC homogeneous (silica gel, 3 CHCl$_3$:MeOH). Anal. Calculated for $C_{15}H_{22}N_4O_3S$: C, 53.21; H, 6.55; N, 16.56. Found: C, 53.33; H, 6.50; N, 16.96.

EXAMPLE 2

Preparation of 3-Deazaadenosine
(5-amino-1-βD-ribofuranosylimidazo[4,5-c]pyridine

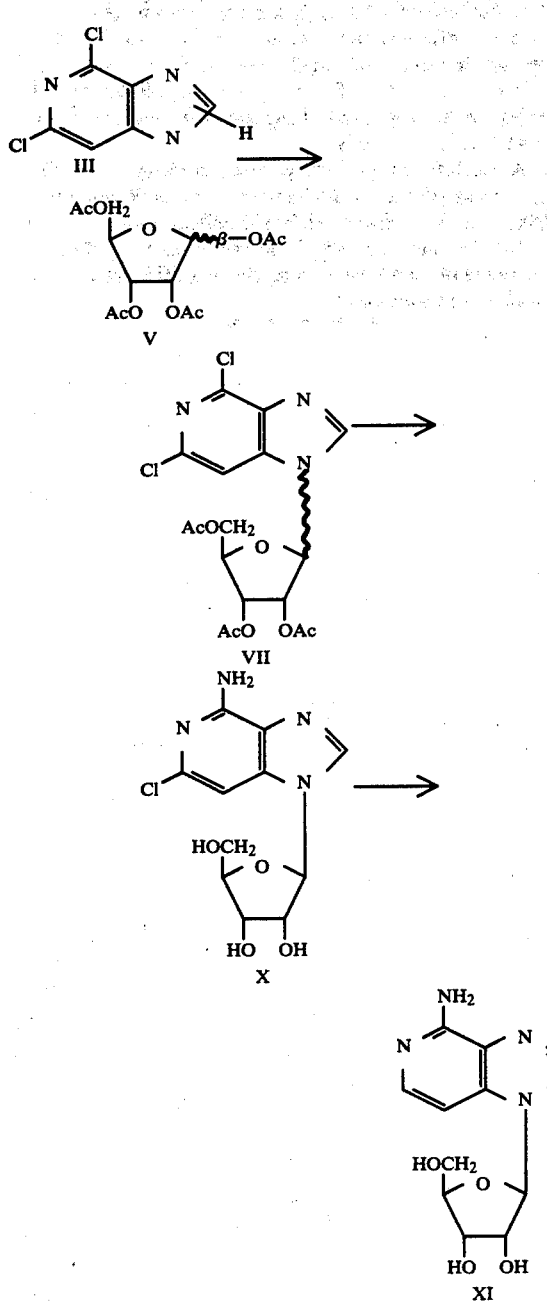

In a fusion reaction, equivalent quantities of the dichloro compound III and 1,2,3,5-tetra-O-acetyl-β-D-ribofuranose (V) gave essentially one nucleoside in high yield with only traces (tlc) of other nucleosidic material. The appearance of all of the methyl signals of the O-acetyl groups below 2 ppm was evidence that this nucleoside had the β- (or trans) configuration with respect to the heterocycle and the 2′-acetoxy group. Treatment of this nucleoside (β-VII) with ethanolic ammonia in a bomb at 140° for 89 hours removed the protecting groups and displaced the 4-chloro group in one step to give 4-amino-6-chloro-1-β-D-ribofuranosylimidazo[4,5-c]pyridine (X) identical to the authenic material (uv, pmr, tlc). Reductive dechlorination of X gave 4-amino-1- β-D-ribofuranosyl [4,5-c]pyridine (3-deazaadenosine, XI) in good yield.

EXAMPLE 3

A comparison as made of the inhibition of AdoHcy hydrolase by 5′-deoxy-5′-S-isobutyl-adenosine, 9-[5′-deoxy-5′-(methylthio)- β-D-arabinofuranosyl]-adenine, 5′-deoxy-5′-(isobutylthio)-3-deazaadenosine, and Nγ-adenosyl-α,γ-diaminobutyric acid, with $I_{50}$'s of >1.0, 0.43, 0.28, and 0.14 mM, respectively, as shown in FIG. 1. 3-Deazaadenosine with an $I_{50}$ of 8 μM remained the most potent inhibitor of AdoHcy hydrolase. 3′-Deazaadenosine was found to be the only competitive inhibitor, with a $K_i$ of 3 μM. The inhibitions caused by Nγ-adenosyl-α, γ-diaminobutyric acid with a $K_i$ of 0.3 mM, 5′-deoxy-(isobutylthio)-3-deazaadenosine with a $K_i$ of 0.04 mM and 9-[5′-deoxy-5′-(methylthio)- β-D-arabinofuranosyl]adenine with a $K_i$ of 0.5 mM were non-competitive in nature (not shown in FIG. 1).

Additionally, the ability of these compounds to inhibit the oncogenic transformation of chick embryo cells induced by RSV-BH was examined. As shown in Table I, 5′-deoxy-5′-(isobutylthio)-3-deazaadenosine was just as effective as 3-deazaadenosine itself in inhibiting focus formation in chick embryo cells infected with RSV-BH. At 0.1 mM both of these compounds, focus formation in RSV-BH infected cells was reduced by 95%, without noticeable effects on the host cells. It is noteworthy that, like other AdoHcy analogs having modifications in the amino acid moiety, it was found not to be hydrolyzed by AdoHcy hydrolase. Neither 3-deaza-AdoHcy nor 9-[5′-deoxy-5′-(methylthio)- β-D-arabinofuranosyl]adenine had any significant effect on focus formation.

TABLE 1

Effects of AdoHcy Analogs on Focus Formation by RSV-BH in Chick Embryo Cells

| Treatment | | No. of Foci* | % Inhibition |
|---|---|---|---|
| None | | 328 | — |
| 3-Deazaadenosine | 0.1 mM | 17 | 95 |
| | 0.03 mM | 106 | 68 |
| 5′-Deoxy-5′-(isobutyl-thio)-3-deazaadenosine | 0.1 mM | 3 | 99 |
| | 0.03 mM | 93 | 72 |
| 3-Deazaadenosyl-homocysteine | 0.1 mM | 276 | 16 |
| | 0.03 mM | 330 | 0 |
| 9-[5′-Deoxy-5′-(methyl-thio)-β-D-arabino-furanosyl]-adenine | 0.1 mM | 298 | 9 |
| | 0.03 mM | 274 | 17 |

*Compounds were added 18 h after infection and foci were counted 7 days later.

EXAMPLE 4

Replication of Gross MLV in mouse embryo cells

Figure 2:
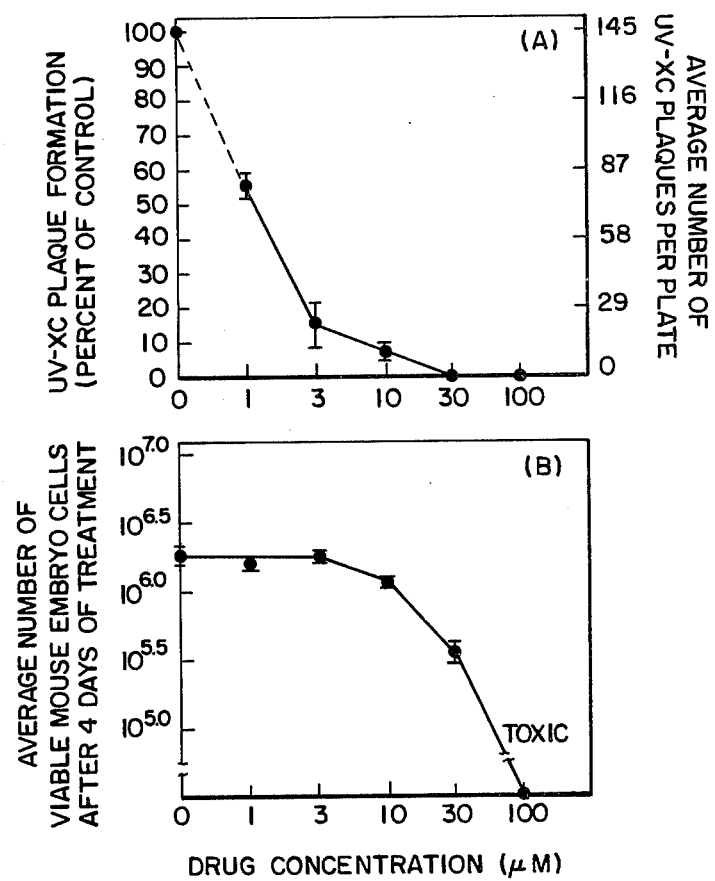
FIG. 2 shows antiviral activity of 5'-deoxy-5'-(isobutylthio)-3-deazaadenosine against Gross MLV in vitro: (A) Inhibition of virus replication in Swiss mouse embryo cells. Each point represents the mean number of UV-XC plaques per culture (triplicate assays)± the standarad deviation. The drug was dissolved in DMSO at the time of virus inoculation and was present throughout the incubation period. (B) Effect of treatment on the multiplication of host cells after 4 days exposure to drug. Each point represents the mean number of viable mouse embryo cells per culture ± the standard deviation. The initial number of cells plated was $3.5 \times 10^5$ cells.

The ability of 5′-deoxy-5′-(isobutylthio)-3-deazaadenosine to inhibit replication of Gross MLV in mouse embryo cells was tested. As seen in FIG. 2A, 5′-deoxy-5′-(isobutylthio)-3-deazaadenosine inhibited the replication of Gross MLV in mouse embryo cells with an 85% inhibition of plaque formation in the indicator XC cells at 3 μM. Complete inhibition of virus replication was obtained at dose levels of 30 to 100 μM, but at these levels cytotoxicity was observed (FIG. 2B). The selectivity ratio (i.e., the highest noncytotoxic concentration of drug over the lowest effective concentration of drug) was about 10.

Whereas the $K_i$ of 5′-deoxy-5′-(isobutylthio)-3-deazaadenosine is about 100 times higher than the $K_i$ of 3-deazaadenosine as inhibitors of AdoHcy hydrolase, the ability of these two compounds to inhibit viral replication is almost equal. 3-Deazaadenosine was found to have a powerful, although reversible, effect on the oncogenic transformation induced by Rous sarcoma virus and on its infectivity. Sensitivity to 3-deazaadenosine was maximal during the phase of virus replication which required the synthesis of viral mRNA and protein and was mimimal during the early period when DNA synthesis was required. The inhibition of virus growth and replication effected by 5'-deoxy-5'-(isobutylthio)-3-deazaadenosine is ascribed as a working hypothesis to two mechanisms: (1) its ability to inhibit AdoHcy hydrolase, inhibition of which would result in a change in a ratio of AdoMet/AdoHcy, which could affect methylation reactions required for viral growth and replication, and (2) its possible direct inhibition of methylases which utilize AdoMet by its intrinsic similarity to AdoHcy.

We claim:

1. 5'-Deoxy-5'-(isobutylthio)-3-deazaadenosine.

2. A method of inhibiting viral activity in chick embryo cells infected with Rous sarcoma virus which comprises mixing with said cells in tissue culture an effective amount of 5'-deoxy-5'-(isobutylthio)-3-deazaadenosine and measuring the resulting inhibition of viral foci in said cells.

3. A method of inhibiting viral activity in mouse embryo cells infected with Gross murine leukemia virus which comprises mixing with said cells in tissue culture an effective amount of 5'-deoxy-5'-(isobutylthio)-3-deazaadenosine and measuring the resulting inhibition of viral foci in said cells.

* * * * *